United States Patent [19]
Holaday

[11] 4,426,378
[45] Jan. 17, 1984

[54] THYROTROPIN RELEASING HORMONE IN THERAPY OF SHOCK AND AS A CENTRAL NERVOUS SYSTEM STIMULANT

[75] Inventor: John W. Holaday, Rockville, Md.

[73] Assignee: The United States of America as represented by the Secretary of the Army, Washington, D.C.

[21] Appl. No.: 252,443

[22] Filed: Apr. 9, 1981

[51] Int. Cl.$^3$ .................... A61K 37/24; C07C 103/52; C07G 7/00
[52] U.S. Cl. ........................... 424/177; 260/112.5 TR
[58] Field of Search ............. 424/177; 260/112.5 T R

[56] References Cited

U.S. PATENT DOCUMENTS

| | | | |
|---|---|---|---|
| 3,746,697 | 7/1973 | Folkers et al. | 260/112.5 TR |
| 3,757,003 | 9/1973 | Folkers et al. | 260/112.5 TR |
| 3,912,705 | 10/1975 | Fujino et al. | 260/112.5 |
| 3,931,139 | 6/1976 | Wissmann et al. | 424/177 |
| 3,959,248 | 5/1976 | Veber et al. | 260/112.5 TR |
| 4,066,749 | 1/1978 | Veber et al. | 260/112.5 TR |
| 4,100,152 | 7/1978 | Fujino et al. | 260/112.5 TR |
| 4,112,073 | 9/1978 | Ono | 260/112.5 TR |
| 4,113,713 | 9/1978 | Schlatter et al. | 260/112.5 TR |

FOREIGN PATENT DOCUMENTS

| | | |
|---|---|---|
| 2611976 | 3/1976 | Fed. Rep. of Germany ... 260/112.5 TR |
| 2449167 | 4/1976 | Fed. Rep. of Germany ... 260/112.5 TR |

Primary Examiner—Dale R. Ore
Attorney, Agent, or Firm—John H. Raubitschek; Werten F. W. Bellamy

[57] ABSTRACT

The therapeutic use of thyrotropin releasing hormone (TRH), its analogs and/or metabolites in the treatment of circulatory shock and/or central nervous system (CNS) ischemic damage is disclosed. Additional evidence of the utility of TRH as a CNS stimulant is revealed.

17 Claims, 7 Drawing Figures

THYROTROPIN RELEASING HORMONE IN THERAPY OF SHOCK AND AS A CENTRAL NERVOUS SYSTEM STIMULANT

CROSS-REFERENCE TO RELATED APPLICATIONS

U.S. patent Application of John W. Holaday Ser. No. 003,699, filed on Jan. 16, 1979 entitled "NARCOTIC ANTAGONISTS IN THE THERAPY OF SHOCK."

BACKGROUND OF THE INVENTION

The field of this invention encompasses the treatment of syndromes which result from an inadequate blood perfusion of vital tissues and evolves in a general stimulant effect of drugs which improve cardiovascular efficiency, often accompanied by behavioral arousal, as well. A more specific aspect of this invention relates to therapy of circulatory shock which is defined as: "The clinical manifestations of an inadequate volume of circulating blood accompanied by physiologic adjustments of the organism to the progressive discrepancy between the capacity of the arterial tree and the volume of blood to fill it" (Blakiston's New Gould Medical Dictionary, 2nd edt., p. 1092, McGraw-Hill, New York, 1956.)

At present, circulatory shock is clinically treated by the administration of fluids such as blood, plasma, volume expanders, or Ringer's lacatate in conjunction with direct-acting cardiovascular drugs such as "Dopamine" which have vasoactive as well as cardiogenic effects. Such therapeutic approach is often ineffective in reversing various forms of shock. Moreover, serious drawbacks limit the clinical utility of such therapeutic regimens. For example, blood typing or intravenous-system setup necessitate a clinical environment which can result in potentially fatal delays between diagnosis and treatment.

Recent pre-clinical experimentation by this inventor has revealed that the body's own opiates, collectively referred to as "endorphins," appear to contribute substantially to the loss of cardiovascular function and resulting shock stress associated with infections, hemorrhage, and spinal-cord injuries. Opiate (narcotic) receptor antagonists are available which pharmacologically oppose endorphin's effects in exacerbating the severity of shock. The therapeutic use of opiate antagonists in treating shock is the subject of a pending patent "Narcotic Antagonists in the Therapy of Shock," Ser. No. 003,699, filed Jan. 16, 1979 by John W. Holaday and Alan I. Faden. Experiments describing the use of one specific opiate antagonist, "Naloxane," are disclosed therein.

Although naloxone is an extremely safe drug with little or no toxic effect, this opiate antagonist also blocks or reverses the analgesic effects of the body's own opiates. Thus, receptor-level opiate antagonists like naloxone may have the adverse effect of intensifying post-traumatic pain by inhibiting endorphin-medicated analgesia even as they improve the shock state and ultimate survival. A drug which reverses shock without affecting an increase in the perception of pain would have obvious advantages.

The use of thyrotropin releasing hormone (TRH) in the therapy of circulatory shock, as disclosed herein, provides a distinctly different approach to this problem. It has been shown that thyrotropin releasing hormone has no effect upon pain perception or opiate-induced analgesia. Thus, TRH and related substances have substantial advantages over existing therapeutic approaches in shock since cardiovascular performance and survival are improved without the potential for enhancing traumatic pain. The absence of any effect of TRH upon opiate analgesia, combined with the opposing behavioral and physiological effects of TRH and opiates, allows for the concurrent administration of opiates, such as morphine and TRH. This would result in the presence of pain relief without the manifestation of the adverse physiological and behavioral side effect of opiates.

Experimental evidence also indicates an arousing or stimulant effect of TRH. When the nervous system is deprived of appropriate blood flow and oxygen, such as may occur following a stroke or myocardial infarction, irreversible nerve cell death may result. The therapeutic administration of TRH to experimental animals subjected to central nervous system (CNS) ischemia results in an improvement in behavioral and physiological parameters. This suggests the potential for TRH and related analogs to minimize neurologic deficits following CNS ischemia such as stroke. Moreover, TRH appears to function as a behavioral stimulant which may improve performance and oppose fatigue.

DESCRIPTION OF THE PRIOR ART

The following comments highlight the significant and material distinctions between the novel methods involved in the instant invention and those described in prior publications. Those publications which are most pertinent are given below and discussed first, with those of lessor interest listed afterwards:

HOLADAY and FADEN, U.S. patent application Ser. No. 003,699 Filed Jan. 16, 1979 entitled "Narcotic Antagonists in the Therapy of Shock." Claims the use of opiate (narcotic) receptor antagonists (e.g. Naloxone) in the treatment of shock. CIP of this case claims use of Naloxone to treat spinal injury, trauma and neurogenic shock.

FUJINO et al U.S. Pat. No. 4,100,152 granted July 11, 1978. Fujino describes synthesis of a TRH analogue which antagonizes anaesthesia and sleep, stimulates spontaneous movement and potentiates dopamine systems.

VEBER et al U.S. Pat. No. 4,066,749, issued Jan. 3, 1978 and FUJINO et al, U.S. Pat. No. 3,912,705, issued Oct. 14, 1975. Both disclose the synthesis of TRH analogues without specification as to pharmacological or physiological function WISSMANN et al U.S. Pat. No. 3,931,139 issued Jan. 6, 1976. Discloses anti-depressant and thyrotropin releasing as well as prolactin-releasing properties.

VERBER et al U.S. Pat. No. 3,959,248 issued May 25, 1976. Describes TRH analogues with effects as anti-depressants and thyrotropin release.

Patents of lesser interest are:

MIKURA et al U.S. Pat. No. 4,167,563 issued Sept. 11, 1979.

German Patent Application Laid-Open (OLS) No. 26 11 976. refers to the use of TRH for the management of impaired consciousness due to functional or organic damage to the brain. This patent application may be distinguished from the instant application in that consciousness or nonconsciousness is only a secondary aspect of TRH function. What is primary to the instant application is that TRH improves blood perfusion to the brain. Consciousness is but one of the many effects of such improved blood flow.

TYSON, U.S. Pat. No. 4,125,605 issued Nov. 4, 1978
ONO, U.S. Pat. No. 4,112,073 issued Sept. 5, 1978

It should be noted that the applicant's invention relates to the non-narcotic therapeutic treatment of "shock" resulting from either the loss of a substantial volume of blood from the body (massive bleeding) or other physiological conditions of the body which prevents the circulation of an adequate volume of blood throughout the arterial system. The non-pertinent nature of all cited references except the first is further highlighted by the fact that blood pressure or cardiovascular function is neither mentioned nor suggested.

The Holaday et al reference cited above refers to the treatment of shock but only through the use of a narcotic receptor antagonist (opiate). TRH, however, is neither a narcotic nor an opiate and performs its functions in an entirely different way than a narcotic (opiate) receptor antagonist.

SUMMARY OF THE INVENTION

Accordingly, there is a need for improved techniques in the treatment of circulatory shock, CNS ischemia, and fatigue. The object of this invention is to provide for this need.

Another object of this invention is to provide a treatment of circulatory shock which is easily administered and rapidly acting, thus minimizing potentially fatal delays in treatment.

Another object of this invention is to treat CNS ischemia resulting from such causes as stroke, cardiac insufficiency, as well as CNS trauma.

Yet another object of this invention is to provide a compound which has no effect upon pain responses and can be coadministered with opiate analgesics.

An additional object of this invention is to provide a drug with CNS-stimulant effects which allows for improved behavioral performance and decreased fatigue.

Another object of this invention is to provide a compound which opposes the toxic effects of organophosphate inhibitors (such as pesticides) of the acetylcholinesterase enzyme function.

Other objects of this invention will become apparent to those having skill in the art.

The objects described above are achieved by the improved cardiovascular, respiratory, and behavioral function caused by this invention which embraces: (1) a method of treating an animal which is suffering from circulatory shock, CNS ischemia, or physiobehavioral depression by administering to said animal a therapeutically effective amount of a drug selected from a group consisting of thyrotropin releasing hormone (TRH), active metabolites of TRH, or TRH analogs and phamaceutically-acceptable salts thereof; and (2) a method of pretreating an animal in order to protect it from shock, CNS ischemia, or to improve physiobehavioral performance by administering to said animal a therapeutically effective amount of a drug selected from a group consisting of thyrotropin releasing hormone (TRH), active metabolites of TRH, or TRH analogs and in addition organic or inorganic pharmaceutical salts, e.g., piperazines, chlorides, etc.

In this disclosure, the term "animal" refers to any organism to include humans which is capable of suffering from circulatory shock, CNS insult, or physiobehavioral depression.

A reasonable extrapolation of the results summarized in this disclosure indicates that TRH, active metabolites of TRH, or TRH analogs and pharmaceutically acceptable salts thereof possess therapeutic value for treating all forms of shock or CNS ischemic damage to include, but not restricted to:
anaphylactic
anaphylactoid
burn
cardiogenic
Hemotogenic (hemorrhagic, wound, hypovolemia)
insulin
neurogenic (nervous, restraint)
septic (vasogenic, endotoxic)
spinal injury (spinal shock, spinal trauma)
stroke (cerebrovascular accident)
toxic (toxic shock syndrome, exotoxic)
traumatic
vasovagal TRH should be effective in improving an acute hypotensive episode that may result from drugs such as anesthetics, etc. or consequential to physiological dysfunction of normal homeostatic mechanisms governing cardiovascular function. Additionally, this group of TRH-related compounds should function as CNS stimulants which improve physiobehavioral performance and decrease fatigue.

The classification of a drug as thyrotropin releasing hormone (TRH), thyrotropin releasing factor (TRH), thyrotropin releasing substance, or any metabolite or analog with all or part of the structural characteristics of the peptide L-pyroglutamyl-L-histidyl-L-prolineamide or any pharmaceutically acceptable salt or derivative thereof is encompassed in this invention. This include, but is not restricted to, the following:

TRH (L-pyroglutamyl-L-histidyl-L-proline amide)
MK771 (pyro-2-aminoadipyl-histidyl-thiazolidine-4-carboxamide)
Histidyl-proline diketopiperazine (and their pharmaceutically acceptable salts)
L-2-ketopiperidine-6-carbonyl-L-Histidyl-L-Thiazolidine-4-carbonyl-B-Alaninamide (L-Kpc-L-His-L-Te-B-AlA-NH$_2$)
Tetrapeptide Amide L-pyroglulamyl-L-histidyl-L-prolyl-B-alaninamide
L-2-oxo-oxazolidine-4-carboxylic acid
L-2-oxo-oxazolidine-4-carbonyl-L-histidyl-L-prolineamide
L-trans-5-methyl-2-oxo-oxazolidine-4-carbonyl-histidyl-L-prolineamide
L-2-oxothiazolidine-4-carbonyl-L-histidyl-L-prolineamide.
3-oxo-5-carboxyperhydro-1,4-thiazine-histidine-proline-NH$_2$
3-oxo-5-carboxyperhydro-1,4-thiazine-histidine-pipecolic acid-NH$_2$
3-oxo-5-carboxyperhydro-1,4-thiazine-histidine-proline-HNCH$_2$CH$_2$Ch$_2$CH$_3$
3-oxo-5-carboxyperhydro-1,4 thiazine-histidine-proline-NHCH$_2$CH$_2$C$_6$H$_5$
$\gamma$-carboxy-$\gamma$-butyrolactone-histidine-proline-NHCH$_2$CH$_2$C$_6$H$_5$
$\gamma$-carboxy-$\gamma$-butyrolactone-histidine-proline-NH$_2$
$\gamma$-carboxy-$\gamma$-butyrolactone-histidine-pipecolic acid-NH$_2$
$\gamma$-carboxy-$\gamma$-butyrolactone-histidine-proline-NH-CH$_3$

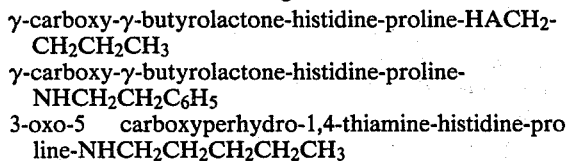

γ-carboxy-γ-butyrolactone-histidine-proline-HACH₂-
CH₂CH₂CH₃
γ-carboxy-γ-butyrolactone-histidine-proline-
NHCH₂CH₂C₆H₅
3-oxo-5 carboxyperhydro-1,4-thiamine-histidine-pro-
line-NHCH₂CH₂CH₂CH₂CH₃

Whether treating an animal once the pathological states have occurred or pretreating animals to prevent their occurrence, any suitable route of administration may be used depending upon the characteristics of the particular drug to be administered. One of ordinary skill could select from the intravenous, intramuscular, subcutaneous, peritoneal, oral, and intrathecal routes of injection. Following intravenous administration, the dose of drug which provides therapeutic efficacy is within a preferred range of 0.001 to 20.0 mg per kg body weight of the animal. Depending upon the route chosen, this dosage range may vary according to its range of availability to effector sites.

Following is a description of the salient features of the laboratory tests which provided experimental evidence for the claim that thyrotropin releasng hormone (TRH) and chemically-related substances are useful in the treatment of circulatory shock, central nervous system ischemia, and function as physiobehavioral stimulants.

IN THE DRAWINGS

EXPERIMENT NO. 1

Tail-artery and external-jugular vein cannulae were implanted in male Sprague-Dawley rats (250–300 g; Zivic-Miller Labs) according to standard surgical techniques. Twenty-four hours later, the arterial cannula were connected to a microtransducer (Narco Biosystems, RP 1500 attached to a Beckman physiograph, type R). This arrangement permitted continuous measurement of blood pressure and heart rate in awake, freely moving rats in their home cages.

Figure 1:
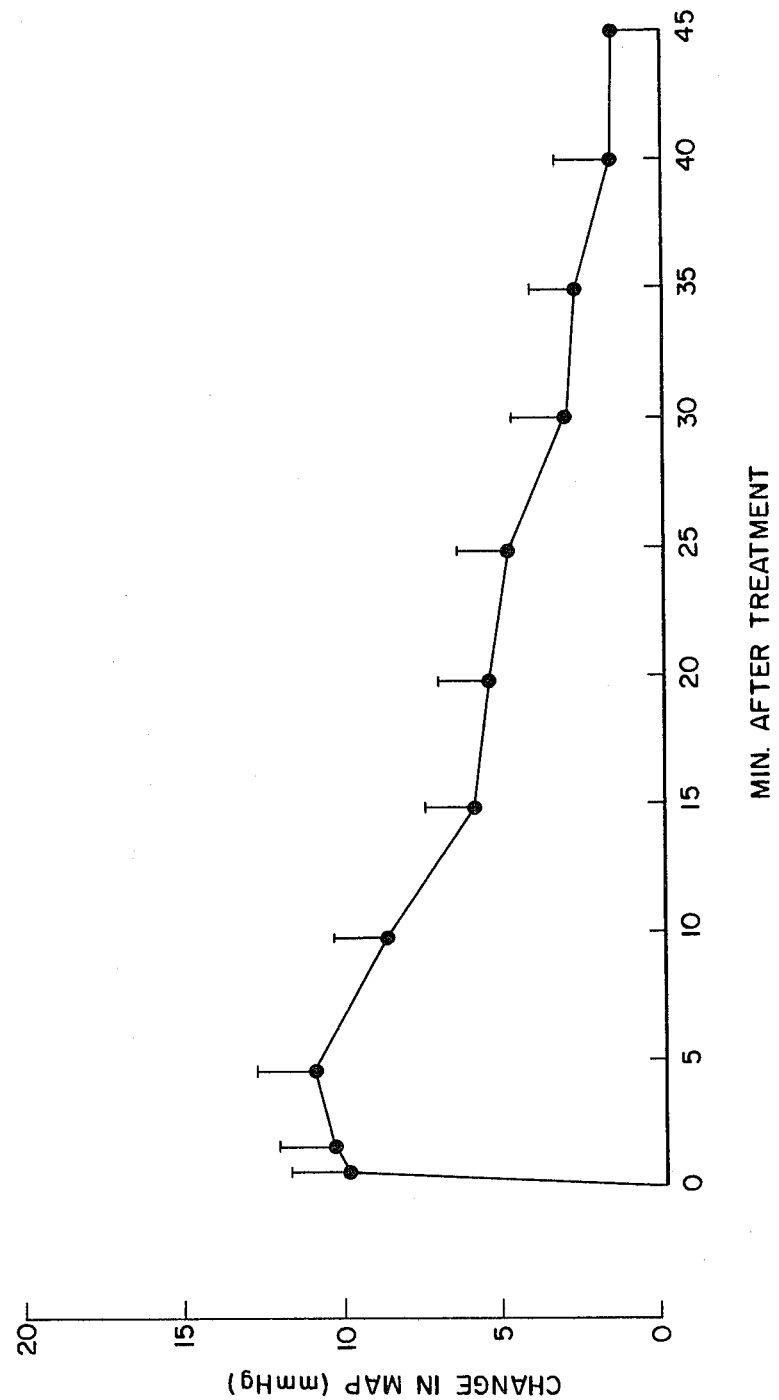
FIGS. 1, 2a and 2b are schematic drawings depicting the results of Experiment No. 1.

In control rats which were not subjected to shock, the cardiovascular effects of intravenous (i.v.) TRH alone were determined. A dose of 2 mg/kg body weight TRH (Beckman Labs) was injected, followed by a cannula flush (0.2 ml saline) to ensure complete drug delivery. Cardiovascular parameters were monitored for two hours. TRH administration caused a significant increase in mean arterial pressure (MAP) of $11.1 \pm 1.5$ mm Hg (n-10, Student's t=7.25, p 0.001), with peak effects observed at 5-minute post-injection and persisting for 30 minutes (FIG. 1).

Figure 2B:
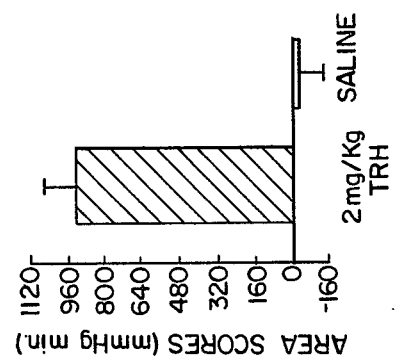
Figure 2A:
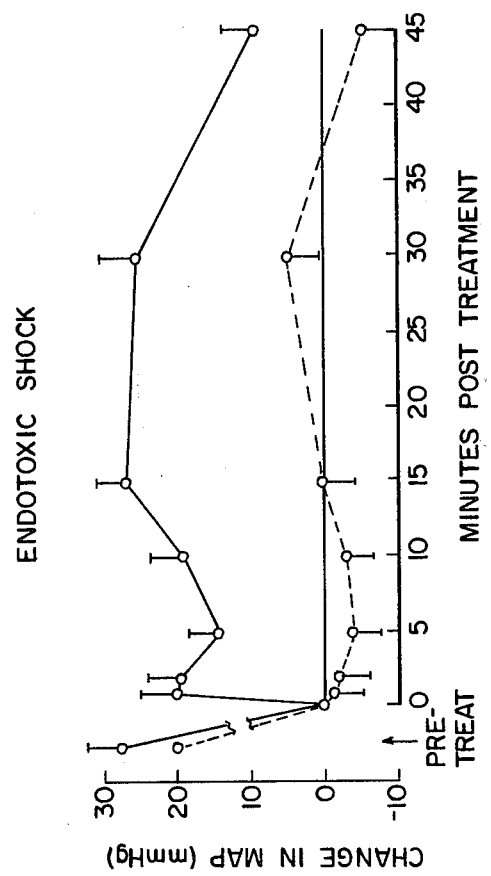

A second group of rats was subjected to endotoxic vasogenic, septic) shock by the i.v. administration of Escherichia coli lipopolysaccharide endotoxin (15 mg/kg; Difco, control #654109). In these animals, MAP fell to 67–70 mm Hg, which was approximately 26% (24 mm Hg) below baseline levels of $92.7 \pm 1.9$ mm Hg (n=22). These rats, randomly divided into two groups, were treated with either i.v. TRH (2 mg/kg, n=13) or an equal volume of i.v. saline (1.0 ml/kg, n=11), followed by a 0.2 ml cannula flush. In contrast to saline treatment, which did not improve blood pressure, TRH-injected animals showed a rapid increase in MAP, which averaged 20–25 mm Hg during the first 30 minutes post-treatment, FIG. 2a. Area scores, FIG. 2b, computed by triangulation of the response-time data, reveal the significant differences between the two treatment groups (Student's t=5.66, p<0.001).

EXPERIMENT NO. 2

Follow-up studies were performed to evaluate other physiological parameters, TRH dose-response characteristics, and the effect of TRH on endotoxic shock survival in the rat. The experiments were conducted identically as described above in Experiment No. 1 for initial endotoxic shock studies, except heart rate, pulse pressure, respiration rate, and behavioral measures were examined following treatment with intravenous saline or TRH (0.2, 0.63, 2.0, 6.34, or 20.0 mg per kilogram body weight). Survival at 2 hours post drug treatment was also assessed. Endotoxin injection resulted in a significant drop in arterial blood pressure. Pressure fell from $98.0 \pm 1.3$(SE) millimeters of mercury (mm Hg) to $70.7 \pm 1.6$ (SE) mm Hg, student's t=13.3, p 0.001. A significant dose-response correlation was obtained when increasing TRH doses, Table 1A, were compared with resulting improvement in MAP 15 minutes following treatment (n=34, r=0.43, p<0.02). TRH injection also increased pulse pressure and heart rate, Table 1A. Respiration rate was increased in a dose-related manner following TRH administration (Table 1A).

Survival following endotoxic shock was significantly improved by TRH treatment (Table 1B). When saline-control rat mortality was compared to mortality in all TRH-treated animals over the 2 hour measurement interval, there was a significant decrease in the lethal effects of endotoxemia produced by a single injection of this substance (Fisher exact probability, p=0.01).

TABLE 1A

CARDIORESPIRATORY VARIABLE
15 MIN. FOLLOWING IV TREATMENT

| | SA-LINE | TRH DOSE (mg/Kg) | | | |
|---|---|---|---|---|---|
| | | 0.20 | 0.63 | 2.00 | 6.34 |
| POPULATION | 8 | 8 | 8 | 8 | 8 |
| CHANGE IN MEAN ARTERIAL PRESSURE (mm Hg) | 13.1 ±4.8 | 21.4 ±5.1 | 20.9 ±5.2 | 24.2 ±5.1 | 35.1 ±3.7 |
| PULSE PRESSURE (mm Hg) | 26.2 ±7.3 | 24.4 ±2.9 | 36.2 ±5.7 | 33.1 ±3.9 | 37.5 ±4.1 |
| HEART RATE (beats/min) | 477.5 ±32.2 | 465.0 ±16.8 | 470.0 ±22.4 | 517.5 ±24.0 | 530.0 ±21.0 |
| RESPIRATORY RATE (breaths/min.) | 128.0 ±12.0 | 107.0 ±6.8 | 109.0 ±4.0 | 125.0 ±6.9 | 147.0 ±4.3 |

TABLE 1B

SURVIVAL 2 HRS FOLLOWING TREATMENT

| | SALINE | TRH DOSE (mg/Kg) | | | |
|---|---|---|---|---|---|
| | | 0.20 | 0.63 | 2.00 | 6.34 |
| ALIVE/DEAD | 4/4 | 7/1 | 8/0 | 7/1 | 8/0 |

EXPERIMENT NO. 3

Figure 3B:
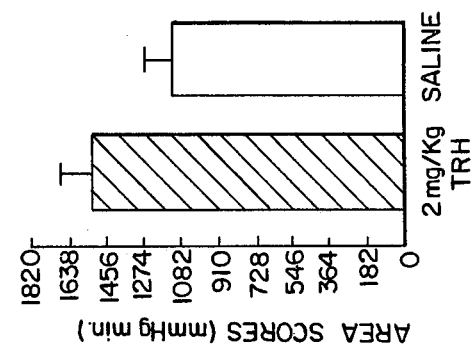
FIGS. 3a and 3b are schematic drawings depicting the results of Experiment No. 3.
Figure 3A:
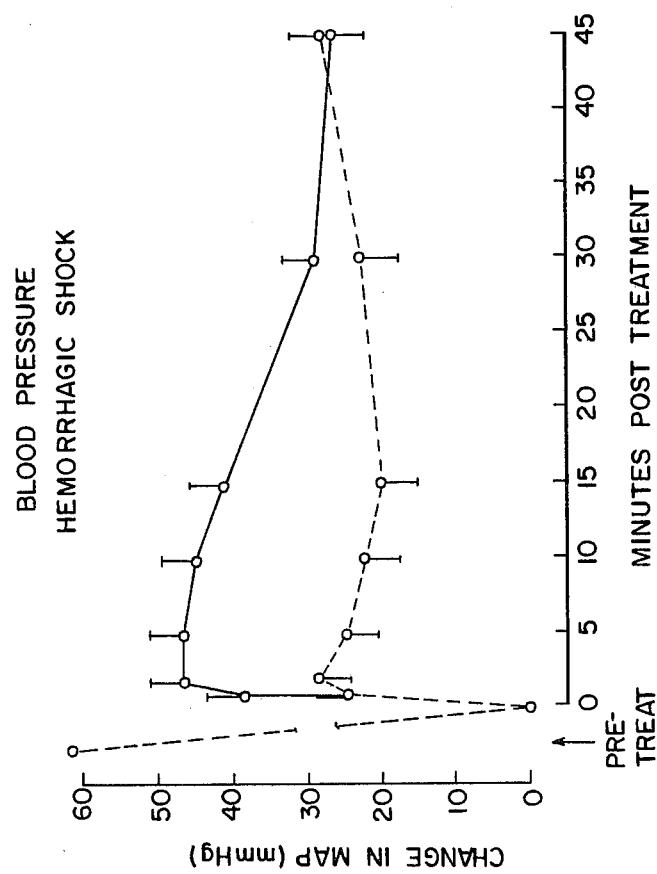

Another group of rats was subjected to hemorrhagic shock according to our previous experimental design. In a total of 27 rats, blood was withdrawn from the indwelling external jugular vein cannula; MAP fell from $96.5 \pm 1.6$ mm Hg to $37.2 \pm 1.0$ mm Hg where it was maintained for 20 minutes. A total of $2.5 \pm 0.1$ mm/100 g (body weight) of blood was removed, a volume approximating 45% of estimated total blood volume. Following the 20 minutes of controlled oligemia, animals were treated with either i.v. TRH (2 mg/kg, m=15) or an equal volume of i.v. saline (1.0 ml/kg, n=12) followed by a 0.2 ml cannula flush. Shed blood was not returned. As seen in FIGS. 3a and 3b, TRH-treated rats experienced a rapid improvement in MAP which was 20–25 mm Hg higher than saline-control rats for the first 15 minutes following injection. The duration of this effect was about 30 minutes, approximately equivalent to the duration of the pressor response to TRH in normotensive rats not subjected to shock, FIG. 3a. In this model, saline-treated rats also experienced an increase in MAP, a consequence of the fluid volume infused. Nevertheless, area scores, FIG. 3b, were significantly greater in TRH-treated animals (Student's t=2.11, p<0.05).

In addition to its effects upon physiological parameters, intravenous TRH also produced a variety of behavioral effects indicative of its action as a CNS stimulant. Wet-dog shaking behavior was observed following doses as low as 0.63 mg per kg; whereas tail-rattling, oral "chewing" stereotypies, and piloerection were frequently observed following doses of 6.34 or 20.0 mg per kg body weight.

EXPERIMENT NO. 4

Figure 4A:
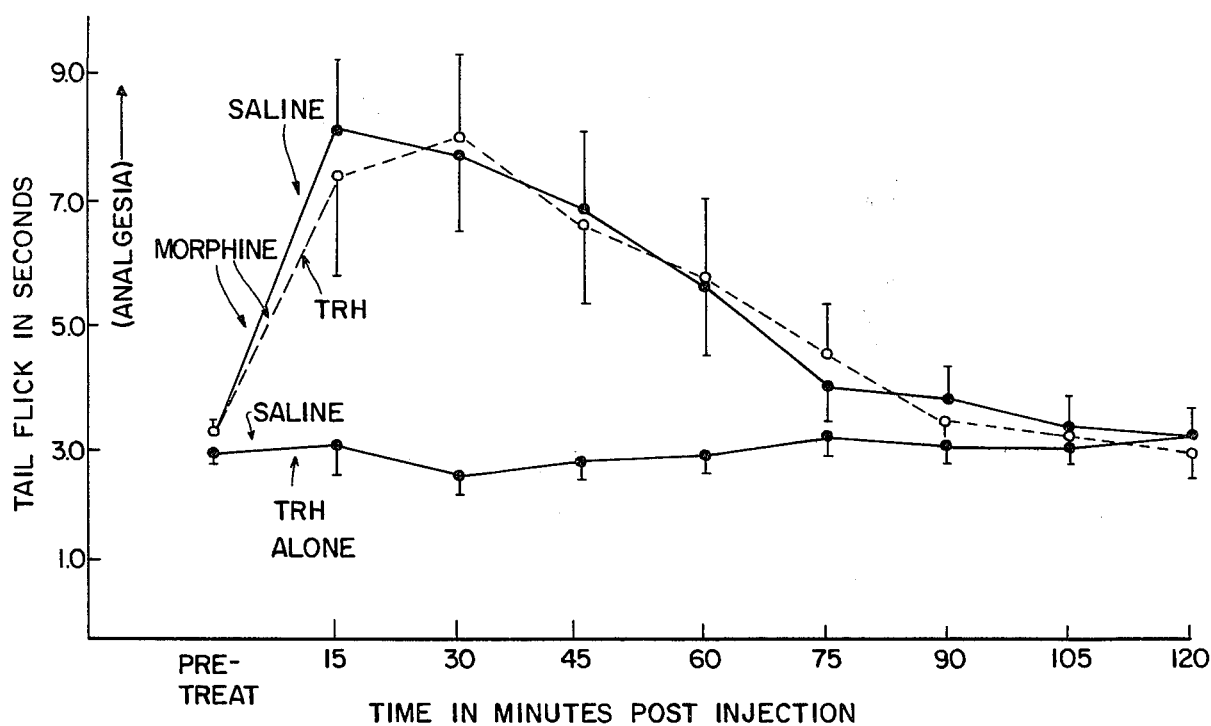
FIGS. 4a and 4b are schematic drawings depicting the results of Experiment No. 4.
Figure 4B:
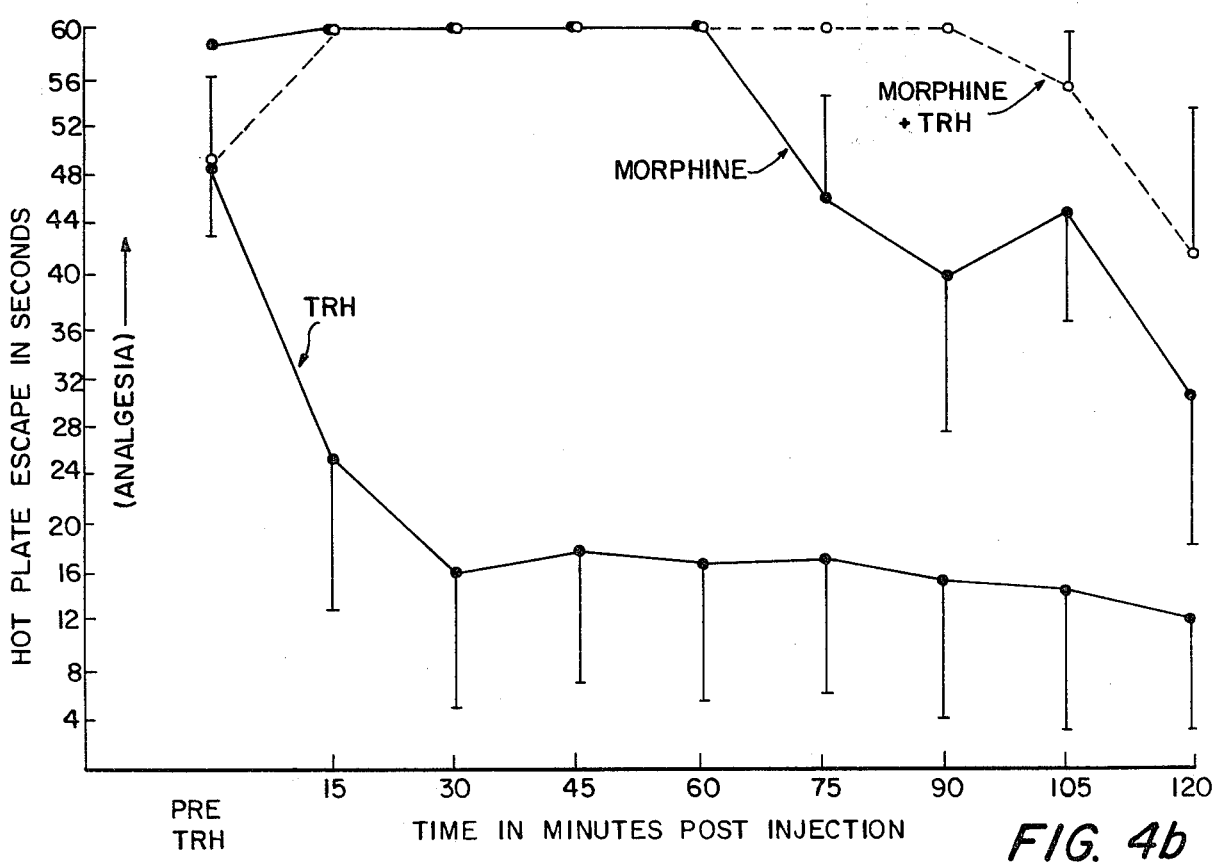

To confirm the lack of effect of TRH upon analgesic responses, an additional group of rats was equipped with intravenous cannulae only. One day later, rats were divided into 3 groups (n=6/group). Group one received TRH alone (2.0 mg/kg—a dose with therapeutic effects in shock), group two received morphine sulfate (4 mg per kg) followed by TRH (2.0 mg per kg), and group three got morphine sulfate alone (4.0 mg per kg). Pain latencies were determined by applying a thermal stimulus to the tail, tail-flick procedure, FIG. 4a, and by measuring how long required for a rat to escape from an enclosure with a heated floor (53° C.), FIG. 4b. Data therein demonstrates no effect of TRH alone on either measure of pain; moreover, TRH did not alter the intensity or duration of morphine-induced analgesia.

CONCLUSIONS

As indicated by the successful reversal of experimental shock states by thyrotropin releasing hormone (supra), ample evidence is provided to indicate that this substance is effective in reversing shock, regardless of how it was induced. This effect seems to be a consequence of a stimulant effect of TRH. Without being bound to any specific hypothesis, it appears that TRH is working directly upon brain sites which regulate autonomic as well as behavioral arousal. The rapid onset of effects following TRH administration suggests a direct action of this hormone which is independent of its physiological role in releasing pituitary thyrotropin and, secondarily, triiodothyronine and/or thyrosin from the thyroid gland although the ultimate release of these substances may also contribute to the therapeutic benefit of TRH.

It is believed that thyrotropin releasing hormone (TRH), its metabolites, or analogs of this compound with varying efficacies would all produce therapeutic effects in animals that are hypotense due to shock, the administration of hypotensive drugs (such as anesthetics), or in animals whose central nervous system function is depressed due to physiological or pharmacological causes such as stroke, myocardial infarction, or depressant drugs. Moreover, the arousing effect of TRH and related substances indicates their possible utility as behavioral stimulants which have the potential to improve performance as well as decrease fatigue.

I claim:

1. A method of antagonizing non-analgesic side effects of exogenous opiates as hypotension, hypothermia, emesis, diminution of gastric motility, pupil constriction, depressed respiratory function in animals which have been treated with one or more opiates which comprises concurrently administering intraveneously to the animal a therapeutically effective amount of a drug selected from the group consisting of Thyrotropin Releasing Hormone (L-pyroglutamyl-1-histidyl-L-proline amide), a derivative of Thyrotropin Releasing Hormone (L-pyroglutamyl-1-histidyl-L-proline amide), and a pharmaceutically-acceptable salt thereof, in combination with an opiate drug.

2. The method of claim 1 wherein the drug is TRH and the opiate drug is morphine.

3. A method of treating an animal suffering from a form of shock selected from the group consisting of anaphylactic, anaphylactoid, burn, cardiogenic, hemistogenic (hemorrhagic, wound), hypovolemic, septic (vasogenic, endotoxic), neurogenic (nervous, restraint), traumatic, and spinal (spinal injury, spinal trauma), insulin, toxic (toxic shock syndrome, exotoxic), vasovagal, and anesthetic which comprises administering intravenously, intramuscularly, subcutaneously, peritoneally, orally or intrathecally to said animal a therapeutically effective amount of a drug which is selected from the group consisting of Thyrotropin Releasing Hormone(L-pyroglutamyl-L-histidyl-L-proline amide), a derivative of Thyrotropin Releasing Hormone(L-pyroglutamyl-1-histidyl-L-proline amide) and a pharmaceutically-acceptable salt thereof.

4. The method of claim 3 wherein the derivative is selected from the group consisting of MK771 (pyro-2-aminoadipyl-histidyl-thiazolidine-4-carboxamide), Histidyl-proline diketopiperazine; Histidyl-proline diketopiperazine; L-2-ketopiperidine-6-carbonyl-L-Histidyl-L-Thiazolidine-4-carbonyl-B-Alaninamide (L-Kpc-L-His-L-Te-B-AlA-NH$_2$); Tetrapeptide Amine L-pyroglulamyl-L-histidyl-L-prolyl-B-alaninamide; L-2-oxo-oxazolidine-4-carboxylic acid; L-2-oxo-oxazolidine-4-carbonyl-L-histidyl-L-prolineamide; L-trans-5-methyl-2-oxo-oxazolidine-4-carbonyl-histidyl-L-prolineamide; L-2-oxothiazolidine-4-carbonyl-L-histidyl-L-prolineamide; 3-oxo-5-carboxyperhydro-1,4-thiazine-histidine-proline-NH$_2$; 3-oxo-5-carboxyperhydro-1,4-thiazine-histidine-pipecolic acid-NH$_2$; 3-oxo-5-carboxyperhydro-1,4-thiazine-histidine-proline-HNCH$_2$CH$_2$CH$_2$CH$_3$; 3-oxo-5-carboxyperhydro-1,4-thiazine-histidine-proline-NHCH$_2$CH$_2$C$_6$H$_5$; $\gamma$-carboxy-$\gamma$-butyrolactone-histidine-proline-NHCH$_2$CH$_2$C$_6$H$_5$; $\gamma$-carboxy-$\gamma$-butyrolactone-histidine-proline-NH$_2$; $\gamma$-carboxy-$\gamma$-butyrolactone-histidine-pipecolic acid-NH$_2$; $\gamma$-carboxy-$\gamma$-butyrolactone-histidine-proline-NH-CH$_3$; $\gamma$-carboxy-$\gamma$-butyrolactone-histidine-proline-HACH$_2$-CH$_2$CH$_2$CH$_3$; $\gamma$-carboxy-$\gamma$-butyrolactone-histidine-proline-NHCH$_2$CH$_2$C$_6$H$_5$; and 3-oxo-5-carboxyperhydro-1,4-thiamine-histidine-proline-NHCH$_2$CH$_2$CH$_2$CH$_2$CH$_3$.

5. The method of claim 3 wherein the drug is Thyrotropin Releasing Hormone(L-pyroglutamyl-L-histidyl-L-proline amide).

6. The method of claim 3 wherein the therapeutically effective quantity of the drug is administered intraveneously between 0.001 mg/kg to 20.0 mg/kg of body weight of the animal.

7. The method of claim 3 wherein the form of shock is selected from the group consisting of anaphylactic, anaphylactoid, burn, cardiogenic, hypovolemic, septic, neurogenic, traumatic and spinal.

8. The method of claim 7 wherein the form of shock is selected from the group consisting of anaphylactic, anaphylactoid, burn, cardiogenic, hypovolemic and septic.

9. The method of claim 7 wherein the form of shock is selected from the group consisting of neurogenic, traumatic and spinal.

10. A method of pretreating an animal in need thereof from a form of shock selected from the group consisting of anaphylactic, anaphylactoid, burn, cardiogenic, hematogenic (hemorrhagic, wound), hypovolemic, septic (vasogenic, endotoxic), neurogenic (nervous, restraint), traumatic and spinal (spinal injury, spinal trauma, insulin, toxic (toxic shock syndrome, exotoxic), vasovagal, and anesthetic which comprises administering intravenously, intramuscularly, subcutaneously, peritoneally, orally or intrathecally to said animal a therapeutically effective amount of a drug which is selected from the group consisting of Thyrotropin Releasing Hormone(L-pyroglutamyl-L-histidyl-L-proline amide), a derivative of Thyrotropin Releasing Hormone (L-pyroglutamyl-1-histidyl-L-proline amide) and a pharmaceutically-acceptable thereof.

11. The method of claim 10 wherein the drug is Thyrotropin Releasing Hormone(L-pyroglutamyl-L-histidyl-L-proline amide).

12. The method of claim 10 wherein the therapeutically effective quantity of the drug is administered intraveneously between 0.001 mg/kg to 20.0 mg/kg of body weight of the animal.

13. The method of claim 12 wherein the drug is Thyrotropin Releasing Hormone(L-proglutamyl-L-histidyl-L-proline amide).

14. The method of claim 10 wherein the derivative is selected from the group consisting of MK 771 (pyro-2-aminoadipyl-histidyl-thiazolidine-4-carboxamide); Histidyl-proline diketopiperazine; L-2-Ketopiperidine-6-carbonyl-L-histidyl-L-Thiazolidine-4-carbonyl-B-alaninamide-(L-Kpc-L-His-L-Te-B-AlA-NH$_2$); Tetrapeptide amide L-pyroglutamyl-L-histidyl-L-prolyl-B-alaninamide; L-2-oxo-oxazolidine-4-carboxylic acid; L-2-oxo-oxazolidine-4-carbonyl-L-histidyl-L-prolineamide; L-2-oxothiazolidine-4-carbonyl-L-histidyl-L-prolineamide; 3-oxo-5-carboxyperhydro-1,4-thiazine-histidine-proline-NH$_2$; 3-oxo-5-carboxyperhydro-1,4-thiazine-histidine-pipecolic acid-NH$_2$; 3-oxo-5-carboxyperhydro-1,4-thiazine-histidine-proline-NNCH$_2$CH$_2$CH$_2$CH$_3$; 3-oxo-5-carboxyperhydro-1,4-thiazine-histidine-proline-NHCH$_2$CH$_2$C$_6$H$_5$; $\gamma$-carboxy-$\gamma$-butyrolactone-histidine-proline-NHCH$_2$CH$_2$C$_6$H$_5$; $\gamma$-carboxy-$\gamma$-butyrolactone-histidine-proline-NH$_2$; $\gamma$-carboxy-$\gamma$-butyrolactone-histidine-pipecolic acid-NH$_2$; $\gamma$-carboxy-$\gamma$-butyrolactone-histidine-proline-NH-CH$_3$; $\gamma$-carboxy-$\gamma$-butyrolactone-histidine-proline-HACH$_2$-CH$_2$CH$_2$CH$_3$; $\gamma$-carboxy-$\gamma$-butyrolactone-histidine-proline-NHCH$_2$CH$_2$C$_6$H$_5$; and 3-oxo-5-carboxyperhydro-1,4-thiamine-histidine-proline-NHCH$_2$CH$_2$CH$_2$CH$_2$CH$_3$.

15. The method of claim 10 wherein the form of shock is selected from the group consisting of anaphylactic, anaphylactoid, burn, cardiogenic, hypovolemic, septic, neurogenic, traumatic, and spinal.

16. The method of claim 15 wherein the form of shock is selected from the group consisting of anaphylactic, anaphylactoid, burn, cardiogenic, hypovolemic and septic.

17. The method of claim 15 wherein the form of shock is selected from the group consisting of neurogenic, traumatic and spinal.

* * * * *